United States Patent [19]
Lee et al.

[11] Patent Number: 5,985,263
[45] Date of Patent: Nov. 16, 1999

[54] SUBSTANTIALLY PURE HISTIDINE-LINKED PROTEIN POLYMER CONJUGATES

[75] Inventors: Seoju Lee, Edison; Charles McNemar, High Bridge, both of N.J.

[73] Assignee: Enzon, Inc., Piscataway, N.J.

[21] Appl. No.: 08/994,621

[22] Filed: Dec. 19, 1997

[51] Int. Cl.⁶ .......................... A61K 38/20; A61K 38/21; A61K 38/02; C07K 1/113

[52] U.S. Cl. ...................... 424/85.2; 424/85.1; 424/85.7; 435/188; 514/2; 530/345; 530/351; 530/409; 530/410

[58] Field of Search .................................. 424/85.1, 85.2, 424/85.4, 85.7, 94.1, 94.3; 530/300, 303, 345, 350, 351, 353, 409, 410, 411; 435/188; 514/2, 3, 12, 21

[56] References Cited

U.S. PATENT DOCUMENTS

| | | | |
|---|---|---|---|
| 4,179,337 | 12/1979 | Davis et al. | 435/181 |
| 4,609,546 | 9/1986 | Hiratani | 514/2 |
| 4,766,106 | 8/1988 | Katre et al. | 514/12 |
| 4,810,638 | 3/1989 | Albarella et al. | 530/409 |
| 4,894,226 | 1/1990 | Aldwin et al. | 424/85.2 |
| 4,897,471 | 1/1990 | Stabinsky | 424/85.7 |
| 4,917,888 | 4/1990 | Katre et al. | 424/85.1 |
| 5,004,605 | 4/1991 | Hershenson et al. | 424/85.6 |
| 5,109,120 | 4/1992 | Ueno et al. | 530/351 |
| 5,122,614 | 6/1992 | Zalipsky | 548/520 |
| 5,281,698 | 1/1994 | Nitecki | 530/351 |
| 5,382,657 | 1/1995 | Karasiewicz et al. | 530/351 |
| 5,468,478 | 11/1995 | Saifer et al. | 424/78.27 |
| 5,539,063 | 7/1996 | Hakimi et al. | 525/403 |
| 5,559,213 | 9/1996 | Hakimi et al. | 530/351 |
| 5,646,242 | 7/1997 | Baker et al. | 530/303 |
| 5,650,234 | 7/1997 | Dolence et al. | 428/447 |
| 5,676,942 | 10/1997 | Testa et al. | 424/85.7 |
| 5,711,944 | 1/1998 | Gilbert et al. | 424/85.7 |
| 5,738,846 | 4/1998 | Greenwald et al. | 424/85.7 |
| 5,747,646 | 5/1998 | Hakimi et al. | 530/351 |

FOREIGN PATENT DOCUMENTS

| | | |
|---|---|---|
| 0 236 987 | 9/1987 | European Pat. Off. . |
| 0 510 356 | 10/1992 | European Pat. Off. . |
| 0 809 996 A2 | 12/1997 | European Pat. Off. ........ A61K 47/48 |
| 0 593 868 B1 | 4/1998 | European Pat. Off. ........ C07K 14/56 |
| WO96/11953 | 4/1996 | WIPO . |

OTHER PUBLICATIONS

Gotoh, Y., et al. Chemical Modification of Silk Fibroin with Cyanuric Chloride–Activated Poly(ethylene glycol): Analysis of Reaction by H–NMR Spectroscop and . . . , Bioconjugate Chem, vol. 4; pp. 554–559; 1993.

Lundblad, R.L., et al. Chemical Reagents for Protein Modification, CRC Press, Inc., vol 1; pp. 105–125; 1988.

Shearwater Polymers, Inc. Catalog, p. 45; Jan. 1996.

Goeddel, D.V. et al., The Structure of Eight Distinct Cloned Human Leukocyte Interferon cDNAs Nature, vol. 290; pp. 20–26; Mar. 5, 1981.

Zalipsky, S. et al., Attachment of Drugs to Polyethylene Glycols Eur. Polym. J., vol. 19, No. 12; pp. 1177–1183; 1983.

Zalipsky S. et al., Evaluation of a New Reagent for Covalent Attachment of Polyethylene Glycol to Proteins Biotechnology and Applied Biochemistry, vol. 15; pp. 100–114; 1992.

Konstek, P., HumanType I Interferons: Structure and Function, Acta Virologica, vol. 38; pp. 345–360; 1994.

(List continued on next page.)

*Primary Examiner*—Jeffrey E. Russel
*Attorney, Agent, or Firm*—Roberts & Mercanti, LLP

[57] ABSTRACT

Substantially pure histidine-linked protein-polymer conjugates and processes for their preparation are disclosed. The processes include contacting a protein with an activated polymer under conditions sufficient to facilitate covalent attachment of at least a portion of the polymer strands on histidine residues of the protein and thereafter substantially separating the histidine-linked conjugates from the remaining reactants.

39 Claims, 3 Drawing Sheets

BIOLOGICAL ACTIVITY IN NORMAL HUMAN SERUM @ 37 C

OTHER PUBLICATIONS

Monkarsh, S.P. et al., Positional Isomers of Monopegylated Interferon alpha–2a: Isolation, Characterization, and Biological Activity, Analytical Biochemistry, vol. 247; pp. 434–440; 1997.

Viscomi, G.C., Structure–activity of Type I Interferons, Biotherapy, vol. 10; pp. 59–86; 1997.

Borokhov et al. Chemical Modification of the Recombinant . . . Biochem. Biophys. Res. Comm. vol. 167, No. 1, pp. 74–80, Feb. 28, 1990.

Kinstler, O.B. et al., Characterization and Stability of N–terminally PEGylated rhG–CSF, Pharmaceutical Res., vol. 13, No. 7; pp. 996–1002; 1996.

FIG-3 BIOLOGICAL ACTIVITY IN NORMAL HUMAN SERUM @ 37 C

SUBSTANTIALLY PURE HISTIDINE-LINKED PROTEIN POLYMER CONJUGATES

BACKGROUND OF THE INVENTION

1. Field of the Invention

The present invention is directed to substantially pure protein-polymer conjugates. In particular, the invention is directed to histidine-linked protein-polymer conjugates and methods of making the same.

2. Description of Related Art

Conjugating biologically-active proteins to polymers has been suggested to improve one or more of the properties of circulating life, water solubility or antigenicity in vivo For example, some of the initial concepts of coupling peptides or polypeptides to polyethylene glycol (PEG) and similar water-soluble polymers are disclosed in U.S. Pat. No. 4,179,337, the disclosure of which is incorporated herein by reference.

Insulin and hemoglobin were among the first therapeutic agents conjugated. These relatively large polypeptides contain several free lysine ε-amino attachment sites. Several polymers could be attached without significant loss of biologic activity.

For many biologically active materials, the conjugation process, however, is not without complications. The conjugation process is not specific with regard to attachment sites. Care must be taken to limit the loss of biological activity caused by the conjugation reaction. For example, if too much of the activated polymer is attached to the target protein or polypeptide, biological activity can be severely reduced or lost. Further, if the wrong linker joining the polymer to the protein is used or if an insufficient amount of polymer is attached to the target, the therapeutic value of the resultant conjugate is rather limited. Often, such conjugates do not demonstrate enough of an increase in the circulating life to compensate for the loss in bioactivity. Problems can also result when a therapeutic moiety's active site (i.e. where groups associated with bioactivity are found) becomes blocked as a result of the polymer attachment. This problem can be difficult to avoid since the polymer and protein are typically joined in solution-based reactions and the polymer conjugation process is not specific with regard to attachment sites. Pre-blocking the active sites with materials such as pyridoxal phosphate has been suggested, but the results have been inconsistent. Lysine-depleted variants of proteins have also been suggested as a way of controlling polymer attachment. This technique, however, is often impractical since it adds significantly to the cost of the final product. The problems are particularly acute with lower molecular weight proteins and peptides. These bioactive materials often have few attachment sites not associated with bioactivity.

In another attempt to avoid the loss of bioactivity following polymer conjugation, granulocyte colony stimulating factor ("G-CSF") was conjugated to mPEG carboxymethyl-N-hydroxy-succinimidyl ester then treated with two molar hydroxylamine (pH 7.3) to remove "unstable" linkers, followed by a pH reduction to 3.5. Kinstler et al., 1996, *Pharmaceutical Res.* 13(7): 996–1002. No description or suggestion of attaining improved G-CSF nor guidance regarding treatment of any other protein conjugates was provided.

Interferons, hereinafter also referred to as IFN's, are a particular example of proteins which could benefit from improved polymer conjugation techniques. See, for example, U.S. Pat. Nos. 4,766,106 and 4,917,888 which describe inter alia beta interferon conjugated with activated polymers including mPEG-2,4,6-trichloro-S-triazine, mPEG-N-succinimidyl glutarate or mPEG-N-succinimidyl succinate. The patentees disclose that covalent modification of the protein is done at a pH of from 5 to 9 and, when the protein is reacted through its lysine residues, covalent modification of the protein is done at a pH of from 8 to 9. Relatively high molar excesses (10, 20 and 50-fold) of the activated polymer are also used.

European Patent Application bearing publication No. 0 236 987 describes reacting alpha and gamma interferons with high molar excesses of alkyl imido ester-activated polyethylene glycols under conditions which preferably include a pH of from approximately 7 to 9. European Patent Application bearing publication No. 0 510 356 describes conjugating alpha interferon with pyridinyl carbonyl and thiocarbonyl activated PEG at a pH of from 7 to 9. There was no mention in these disclosures that amino acids other than lysine were involved in the conjugation or that it would be advantageous to do so.

WO96/11953 reports that conjugates were prepared by reacting a protein, exemplified by consensus IFN, with a polymer, at an acid pH (pH 4) using a reductive alkylation reaction for the selective attachment of polymer, e.g., PEG, to the N-terminal. WO96/11953 states that this reaction selectively prevents linkage to lysine epsilon amino groups, while favoring linkage with the N-terminal alpha amino group. WO96/1 1953 also describes a two-step pH treatment process wherein G-CSF is reacted with a PEG at pH 8.0, followed by reduction of pH to pH 4.0, simply as a prelude to loading the product onto a separation column. WO96/11953 does not teach or suggest the advantages of an acylation reaction to selectively attach polymers to IFN residues other than the N-terminal or lysines.

In view of the above-described disclosures, it is believed that additional improvements in interferon-polymer conjugates are desirable in order to address various shortcomings. The present invention provides additional improvements to the field and thus addresses these shortcomings.

SUMMARY OF THE INVENTION

In one aspect, the present invention includes substantially pure protein-polymer conjugates. The conjugates include a protein, such as an alpha interferon, covalently conjugated to a polymer, such as a polyethylene glycol, at a histidine (His) residue of the protein. In the case of an alpha interferon, the histidine is preferably the histidine 34. Preferably, the alpha interferon is interferon α2b and the conjugates contain about one polymer strand per alpha interferon molecule. Histidine-linked mono-polymer conjugates of other proteins, such as IL-10, are also included as part of the invention. Compositions containing the preferred mono-polymer His-linked conjugates may also contain minor amounts of other mono-PEG-protein species, if desired.

In another embodiment of the invention, methods of preparing substantially pure protein-polymer conjugates are provided. In particular, the methods are directed to preparing the protein-histidine residue linked polymer-conjugates. The methods include forming a plurality of protein-polymer conjugate species or positional isomers by reacting a protein such as alpha interferon, with a sufficient amount of suitably activated polymer under conditions sufficient to facilitate covalent attachment of protein molecules to activated polymer strands and thereafter substantially isolating the conjugated species or positional isomers in which the His linkage between the protein and polymer is established from the remaining conjugate species. In one preferred aspect of this embodiment, the activated polymer is a benzotriazole carbonate-activated polymer. In an alternative aspect, the activated polymer is an oxycarbonyl-oxy-N-dicarboximide-activated polymer such as succinimidyl carbonate (SC-PEG). These activated polymers allow the artisan to form a reaction pool in which a substantial portion of the conjugates include the polymer strand covalently linked to a histidine residue on the alpha interferon rather than on a lysine residue or N-terminus.

Some of the conditions which allow the protein His positional isomer, such as the αIFN His34 isomer, to be formed in relatively high amounts vis à vis the other positional isomers include conducting the acylating polymer conjugation reaction within a particular pH range, i.e. preferably less than about 7 and more preferably from about 4.5 to about 6.8. This facilitates preferential covalent attachment of at least a portion of the polymer strands to histidine residue amino groups of the protein. The desired, substantially pure, protein conjugates are then preferably isolated from the remaining protein conjugates in the reaction pool using chromatography columns such as gel filtration followed by cation exchange or anion exchange followed by cation exchange.

Suitable alpha-interferons include recombinant and non-recombinant alpha-interferons isolated from mammals. The polymer portion of the conjugate is preferably a polyalkylene oxide (PAO), such as a monomethoxy polyethylene glycol (mPEG). In alternative embodiments, other substantially non-antigenic polymers can also be used. The polymers preferably have a molecular weight of from about 200 to about 35,000.

The invention also includes methods of treating various medical conditions such as alpha-interferon susceptible conditions in mammals. In this aspect, the treatment includes administering an effective amount of a composition containing the protein conjugates described herein to mammals requiring such therapy.

For purposes of the present invention, the term "positional isomer" shall be understood to generally describe a conjugate having a polymer strand attached at one of the available amino acid residues. Specific positional isomers are described herein with reference to the amino acid residue attachment point. For example, the protein-Lys31-polymer positional isomer denotes a mono-polymer conjugate of a protein having the polymer attached at the Lys31. Other positional isomers, i.e., those conjugates having the polymer attached elsewhere on the protein would be similarly designated.

For purposes of the present invention, the term "substantially pure" shall be understood to denote the level or degree of purity of a composition containing a desired positional isomer of a protein-polymer conjugate. Depending upon the protein conjugated and the conjugate separation technique employed, compositions in accordance with the present invention will be deemed to be substantially pure if they contain a majority of the desired positional isomer. Preferably, the compositions contain at least about 60% and more preferably at least about 80% of the desired positional isomer.

Also for purposes of the present invention, "substantially separating" shall be understood to describe a part of the inventive process in which a desired positional isomer is recovered from the spectrum of positional isomers as a result of using (preferably) high performance liquid chromatography. The resulting isolates contain substantially pure isolates of the desired positional isomer and possibly minor amounts, e.g. less than 15%, of other positional isomers.

As a result of the present invention, it has been unexpectedly found that additional improvements in protein-polymer conjugate compositions are possible. For example, it is now possible to obtain substantially pure positional isomers, including those having relatively high levels of bioactivity in relatively high yields. In the case of αIFN, the preferred positional isomers, i.e. mono-polymer-His34 linked IFNα-2b conjugates, demonstrate unexpectedly high levels of bioactivity relative to not only native alpha interferon but also relative to other positional isomers. The other positional isomers, i.e., those conjugates having the polymer attached elsewhere on the interferon, such as the N-terminus or a lysine amino group, often demonstrate lower but nonetheless useful amounts of bioactivity and may be included in some inventive compositions in minor amounts.

It has also been surprisingly found that when the conjugation reaction includes certain activated polymers, such as benzotriazole carbonate (BTC) activated polymers, unexpectedly high amounts of histidine-linked positional isomers are formed.

For a better understanding of the present invention, reference is made to the following description and drawings.

DETAILED DESCRIPTION OF THE INVENTION

1. Proteins

For purposes of the present invention the term "protein" shall be understood to encompass not only proteins, but also polypeptides, enzymes, peptides and the like having at least one available histidine for polymer attachment. Furthermore, the proteins contemplated for use herein are not limited to those having physiological or pharmacological activities. For example, also included are enzyme conjugates which are able to catalyze reactions in organic solvents. Likewise, some inventive polymer conjugates are also useful as laboratory diagnostics. Two key features of all of the conjugates is that they are preferably linked via His residues and they maintain at least some portion of the activity associated with the unmodified protein.

Proteins, polypeptides and peptides of interest include, but are not limited to, hemoglobin, serum proteins such as blood factors including Factors VII, VIII, and IX; immunoglobulins, cytokines such as interleukins, i.e. IL-1 through IL-13, α-, β- and γ-interferons, preferably α-interferon described in more detail below, colony stimulating factors including granulocyte colony stimulating factors, platelet derived growth factors and phospholipase-activating protein (PLAP). Other proteins of general biological or therapeutic interest include insulin, plant proteins such as lectins and ricins, tumor necrosis factors and related proteins, growth factors such as transforming growth factors, such as TGFα's or TGFβ's and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, Igm, IgA, IgD and fragments thereof Some proteins such as the interleukins, interferons and colony stimulating factors also exist in non-glycosylated form, usually as a result of using recombinant techniques. The non-glycosylated versions are also among the proteins of the present invention.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubin oxidase. Carbohydrate-specific enzymes of interest include glucose oxidases, glucodases, galactosidases, glucocerebrosidases, glucouronidases, etc.

Also included herein is any portion of a polypeptide demonstrating in vivo bioactivity. This includes histidine-containing amino acid sequences, antibody fragments, single chain antigen binding proteins, see, for example U.S. Pat. No. 4,946,778, disclosure of which is incorporated herein by reference, binding molecules including fusions of antibodies or fragments, polyclonal antibodies, monoclonal antibodies and catalytic antibodies.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained from transgenic animals, i.e., mice, pigs, cows, etc., wherein the proteins are expressed in milk, blood or tissues. Transgenic insects and baculovirus expression systems are also contemplated as sources. Moreover, mutant versions of proteins, such as mutant interferons are also within the scope of the invention.

Other proteins of interest are allergen proteins such as ragweed, Antigen E, honeybee venom, mite allergen, and the like.

One preferred protein is alpha interferon described in more detail below. The foregoing is illustrative of the proteins which are suitable for the present invention. It is to be understood that those proteins, as defined herein, not specifically mentioned but having an available histidine group are also intended and are within the scope of the present invention.

It will also be understood by the artisan of ordinary skill that the invention includes proteins, as defined herein, which have been specifically engineered to include a histidine for use as a polymer attachment site.

In another aspect of the invention, the conjugated moiety is a non-protein-based compound such as an organically synthesized molecule which either naturally contains an amino or other suitable linking group for attaching a polymer or has been modified using standard synthetic techniques to include a histidine, tyrosine, imidazole or similar nitrogen or amine-containing group for attaching a polymer as described herein.

2. Intererons

In those aspects of the invention where the protein is an interferon (IFN), it will be understood that the protein can be prepared or obtained from a variety of sources including recombinant techniques such as those using synthetic genes expressed in *E. coli*. See also Pestka, "Interferon α" in *Human Cytokines*, Blackwell Scientific Publications 1–16 (1992), the disclosure of which is incorporated herein by reference. In addition, the IFN is preferably an αIFN and can also be a mammalian source extract such as human, ruminant or bovine αIFN. One particularly preferred IFN is IFNα-2b, a recombinantly-made product of the Schering Corp., Kenilworth, N.J.

The term "interferon" or "IFN" as used herein means the family of highly homologous proteins that inhibit viral replication and cellular proliferation and modulate immune response. Human interferons are grouped into three classes based on their cellular origin and antigenicity: α-interferon (leukocytes), β-interferon (fibroblasts) and γ-interferon (13 cells). Recombinant forms of each group have been developed and are commercially available. Subtypes in each group are based on antigenic/structural characteristics. At least 24 interferon alphas (grouped into subtypes A through H) having distinct amino acid sequences have been identified by isolating and sequencing DNA encoding these peptides. See also Viscomi, 1996 *Biotherapy* 10:59–86, the contents of which are incorporated herein by reference. The terms "α-interferon", "alpha interferon", "interferon alpha" and "human leukocyte interferon" are used interchangeably in this application to describe members of this group. Both naturally occurring and recombinant α-interferons, including consensus interferon such as that described in U.S. Pat. No. 4,897,471, the contents of which are incorporated herein by reference, may be used in the practice of the invention.

The purification of interferon alpha from human leukocytes isolated from the buffy coat fraction of whole blood is described in U.S. Pat. No. 4,503,035. Human leukocyte interferon prepared in this manner contains a mixture of human leukocyte interferons having different amino acid sequences. Purified natural human α-interferons and mixtures thereof which may be used in the practice of the invention include but are not limited to Sumiferon® interferon alpha-n1 available from Sumitomo, Japan, Wellferon® interferon alpha-n1 (Ins) available from Glaxo-Wellcome Ltd., London, Great Britain, and Alferon® interferon alpha-n3 available from the Purdue Frederick Co., Norwalk, Conn.

The advent of recombinant DNA technology applied to interferon production has permitted several human interferons to be successfully synthesized, thereby enabling the large-scale fermentation, production, isolation, and purification of various interferons to homogeneity. Recombinantly produced interferon retains its in vitro and in vivo antiviral and immunomodulatory activities. It is also understood that the recombinant techniques could also include a glycosylation site for addition of a carbohydrate moiety on the recombinantly-derived polypeptide.

The construction of recombinant DNA plasmids containing sequences encoding at least part of human leukocyte interferon and the expression in *E. coli* of a polypeptide having immunological or biological activity of human leukocyte interferon are disclosed in U.S. Pat. No. 4,530,901 and European Patent No. EP 0 032 134.

The construction of hybrid α-interferon genes containing combinations of different subtype sequences (e.g., A and D, A and B, A and F) is disclosed in U.S. Pat. Nos. 4,414,150, 4,456,748 and 4,678,751. Typical suitable recombinant α-interferons which may be used in the practice of the invention include but are not limited to interferon alpha-2b such as Intron® A available from Schering Corporation, Kenilworth, N.J., interferon alpha-2a such as Roferon® A available from Hoffinann-La Roche, Nutley, N.J., and Infergen® available from Amgen, Thousand Oaks, Calif.

Alternate embodiments, where the foreign αIFN is not completely autologous, may be also used if desired. A key, however, is that the non-autologous αIFN has sufficient bioactivity or αIFN effect such as antiviral activity in the target mammal. Other substances including αIFN fractions or predecessor polypeptides can also be included in the conjugates of the present invention. As used herein, "α-IFN effect in mammals" means in vivo activity corresponding to that observed with αIFN's. These substances are prepared by using techniques known to those of ordinary skill in the art such as tissue culture, extraction from animal sources or by recombinant DNA methodologies. Transgenic sources of αIFN and related moieties are also contemplated. Such materials are obtained from transgenic animals, e.g. mice, pigs, cows, etc. where the αIFN protein is expressed in milk blood, or other tissues. The method by which the αIFN is prepared for the conjugates of the present invention is not limited to those described herein. For purposes of the present invention, the αIFN's are preferred because of their biochemical and serological properties. In particular, αIFN has documented antiviral properties and diffuses more effectively into the bloodstream than other interferons.

3. Non-Antigenic Polymers

To conjugate the protein to polymers such as poly (alkylene oxides), one of the polymer hydroxyl end-groups is converted into a reactive functional group which allows conjugation. This process is frequently referred to as "activation" and the product is called an "activated" polymer or activated poly(alkylene oxide). Other substantially non-antigenic polymers are similarly "activated" or functionalized.

In accordance with the present invention, the activated polymers are reacted with a protein such as αIFN so that the polymer attachment occurs preferably at amino groups on histidines, and, to a lesser extent, at ε-amino groups of lysines and the N-terminal amino group. Free carboxylic acid groups, suitably activated carbonyl groups, oxidized carbohydrate moieties and mercapto groups if available on the protein can also be used as supplemental attachment sites, if desired.

In a preferred aspect of the invention, urethane (carbamate) linkages are preferably formed between a histidine amino group residue of the protein and the activated polymer. In one preferred aspect of the invention, the activated polymer is a benzotriazole carbonate-activated polymer such as those described in U.S. Pat. No. 5,650,234, the disclosure of which is incorporated herein by reference. In an alternative aspect, the urethane linkage is formed using a terminal oxycarbonyl-oxy-N-dicarboximide group such as a succinimidyl carbonate group. Alternative activating groups include N-succinimide, N-phthalimide, N-glutarimide, N-tetrahydrophthalimide and N-norborene-2,3-dicarboxide. These urethane-forming groups are described in U.S. Pat. No. 5,122,614, the disclosure of which is hereby incorporated by reference. When used as a part of the invention, these preferred activated polymers allow the artisan to form a plurality of protein-polymer conjugates which may or may not include the entire spectrum of positional isomers. The aggregate collection of conjugates formed in the solution-based reaction, however, will contain a significant portion of the conjugates which include the polymer strand covalently linked to a histidine residue on the target protein, i.e. alpha interferon, with lesser amounts of lysine residue linked or N-terminus linked polymer strands.

Among the substantially non-antigenic polymers, mono-activated, alkoxy-terminated polyalkylene oxides (PAO's), such as monomethoxy-terminated polyethylene glycols (mPEG's) are preferred; bis-activated polyethylene oxides (glycols) are also contemplated for purposes of cross-linking proteins or providing a means for attaching other moieties such as targeting agents for localizing the protein-polymer conjugate in a particular area such as, for example, the liver.

Suitable polymers will vary substantially by weight. Polymers having molecular number average weights ranging from about 200 to about 35,000 are usually selected for the purposes of the present invention. Molecular weights of from about 1,000 to about 25,000 are preferred and 2,000 to about 20,000 are particularly preferred.

The polymeric substances included are also preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. In addition to MPEG, $C_{1-4}$ alkyl-terminated polymers are also useful.

As an alternative to PAO-based polymers, effectively non-antigenic materials such as dextran, polyvinyl pyrrolidones, polyacrylamides such as HPMA's -hydroxypropylmethacrylamides, polyvinyl alcohols, carbohydrate-based polymers, copolymers of the foregoing, and the like can be used. Those of ordinary skill in the art will realize that the foregoing list is merely illustrative and that all polymer materials having the qualities described herein are contemplated. For purposes of the present invention, "substantially or effectively non-antigenic" means all materials understood in the art as being nontoxic and not eliciting an appreciable immunogenic response in mammals.

4. Reaction Conditions

Conjugation reactions, sometimes referred to as PEGylation reactions, are often carried out in solution without regard to where the polymer will attach to the protein. Such techniques are also usually carried out at slightly alkaline pH's, i.e. pH 7+ to about 9 for conjugating αIFNs. A key to the present invention, however, is that in certain instances, such as with αIFNs, the retained protein bioactivity can be maximized if a single polymer strand is attached to a histidine rather than a lysine or the N-terminus. In the case of αIFNs, and a IFN 2b in particular, the preferred attachment point is His34. It will be appreciated by the artisan that although various species of the αIFN may or may not have a histidine at amino acid 34, the reaction conditions will nonetheless preferably provide at least some positional isomers containing a polymer attached at an available histidine. The artisan will also appreciate that for proteins other than αIFN, the optimum histidine residue for polymer attachment will be determinable without undue experimentation.

The processes of the present invention therefore include:

1) reacting a solution containing a sufficient amount of a protein such as an alpha interferon with a sufficient amount of a suitably activated polymer, such the preferred benzotriazole carbonate-activated or oxycarbonyl-oxy-N-dicarboximide-activated polymers under conditions sufficient to facilitate covalent attachment of the protein to the activated polymer and form a plurality of protein-polymer conjugates; and 2) substantially separating the protein-polymer conjugates containing a polymer conjugated to a histidine residue of the protein from the plurality of remaining protein-polymer conjugates.

In preferred aspects when the protein is αIFN-2b, the substantially pure compositions substantially contain a polymer conjugated to the His34 of the αIFN-2b.

The reaction is conducted at a pH which is sufficient to facilitate covalent attachment of at least a portion of the polymer strands to a histidine found on the target protein. In particular, the pH is preferably be slightly acidic, i.e. less than about 7.0; more preferably, less than about 6.8 and most preferably in the range of from about 4.5 to about 6.8.

The reaction conditions for effecting conjugation further include conducting the attachment reaction with from about equi-molar to about a relatively small molar excess of the activated polymer with respect to the protein. In this regard, the process can be carried out with about 1–25-fold molar excess of polymer; preferably about 1.5–7-fold molar excess of polymer and most preferably about 1.75–5-fold molar excess of polymer. It will be understood that, depending upon the preferences of the artisan, the activated polymer may be added as a solid or in solution to the target protein. The conjugation reaction can be carried out over a relatively wide temperature range, e.g. about 0–25° C. The reaction time will also vary according to the preference of the artisan and can range from less than one hour to twenty-four hours or even longer, depending upon the activated polymer selected. Quenching of the reaction is optional. These reaction conditions provide a mixture of protein-polymer positional isomers which unexpectedly contain relatively high amounts of His-positional isomers. Preferably, each isomer contains a single polymer strand attached to the protein via an amino acid residue. In alternative embodiments, there can be more than one strand of polymer attached as a result of the conjugation process. Solutions containing these multi-stranded polymer conjugates are also useful as is or can be further processed to separate the conjugates on the basis of molecular weight to obtain mono-polymer conjugates.

5. Isolation Of Mono-Peg Conjugates

Although the inventive process produces a substantial amount of conjugates having a single polymer strand, conjugates having varying degrees of polyalkylene oxide substitution and thus molecular weight are also generated. Residual unconjugated PAO's and proteins can also be present. This mixture is typically in a reaction buffer containing one or more of phosphate, chloride and bicarbonate anions. The PAO, protein and conjugate mixture is preferably fractionated in a buffer solution containing from about 1 to about 10 mg/ml protein conjugates. Suitable fractionating solutions have a pH of from about 7.0 to about 9.0 and preferably from about 7.5 to about 8.5. The solutions preferably contain one or more buffer salts selected from KCl, NaCl, $K_2HPO_4$, $KH_2PO_4$, $Na_2HPO_4$, $NaH_2PO_4$, $NaHCO_3$, $NaBO_4$, $(NH_4)_2CO_3$ and glycine NaOH. Sodium phosphate buffers are preferred.

Depending upon the reaction buffer, the protein-polymer conjugate containing solution may first have to undergo buffer exchange/ultrafiltration. For example, αIFN conjugate solutions can be ultra filtered across a low molecular weight cut-off(10,000 to 30,000 Dalton) membrane which will also remove most surfactants, if present, as well.

The fractionation of the conjugates into desired species based on weight is preferably carried out using an anion exchange medium. Such media are capable of selectively binding those protein-polymer conjugates having a predetermined i.e. one or more polymer strands, excess polymer and unmodified protein. This fractionation occurs since the protein molecules of various degrees of substitution will have isoelectric points which vary in a somewhat predictable fashion. For example, the isoelectric point of proteins is determined by the number of available amino groups available on the surface of the protein. These amino groups also serve as the point of attachment of polyalkylene oxide conjugates. Therefore, as the degree of substitution of polyalkylene oxide increases, the isoelectric point decreases, and the ability of the conjugate to bind to an anion exchange resin weakens. Gel filtration HPLC can also be used to remove higher molecular weight (multi-stranded) conjugates.

The use of strongly polar anion exchange resins is especially preferred for the method of the present invention. For this reason, quaternary amine coated anion exchange resins are utilize. The quaternary amine resin may be coated onto either a polymeric or silica matrix; however, polymeric matrices are preferred. A number of tetramethylamine, or quaternary methylamine, anion exchange resins are commercially available, coated onto the support matrices. Included among the commercially available quaternary anion exchange resins suitable for use with the present invention are Q-HD available from Bio-Sepra, QA TRISACRYL® and QMA-SPHEROSIL®, quaternary amine resins coated onto a polymer matrix, manufactured by IBF of Garenne, France, for Sepracor, Inc. of Marlborough, Mass.; TMAE650M®, a tetramethylamino ethyl resin coated onto a polymer matrix, manufactured by EM-Separators of Gibbstown, N.J.; QAE550C®, and SUPERQC®, each a quaternary amine resin coated onto a polymer matrix and manufactured by TosoHaas of Montgomeryville, Pa. QMA Accell, manufactured by Millipore of Miliford, Mass. and PEI resins manufactured by JT Baker of Phillipsburg, N.J., may also be used.

The anion exchange resin is packed in the column and equilibrated by conventional means. A buffer having the same pH and osmolality as the conjugated protein solution is used. The conjugate-containing solution is then adsorbed onto the column. At the completion of the loading, a gradient flow of an elution buffer with increasing salt concentrations is applied to the column to elute the desired fractions of polyalkylene oxide-conjugated protein. The fractions are of essentially uniform molecular weight and degree of substitution. Separation of the various positional isomers, however is not effected during this type of separation.

Depending upon the protein, preferred conjugate fractions have 1–4 polymer strands per protein molecule. More preferably, the fraction contains about 1–2 and, most preferably, about 1 polymer strand per protein molecule. The elution buffer preferably contains one or more salts selected from KCl, NaCl, $K_2HPO_4$, $KH_2PO_4$, $NaHPO_4$, $NaH_2PO_4$, $NaHCO_3$, $NaBO_4$ and $(NH_4)_2CO_3$. These fractions are substantially free of other conjugates. Any unconjugated species can then be backwashed from the column by conventional techniques.

Techniques utilizing multiple isocratic steps of increasing concentration can also be used. Multiple isocratic elution steps of increasing concentration will result in the sequential elution of protein-polymer conjugates. The degree of polymer conjugation within each fraction will be substantially uniform. However, the degree of polymer conjugation for each fraction will decrease with elution time. Ion exchange purification of the conjugates can also be carried out with, for example, a Q-HD Column from BioSepra, Inc. along with a dilute sodium phosphate solution. For example, samples containing PEG-IFN samples are washed with 10 mM $NaPO_4$ to remove any unreacted PAO and thereafter a step gradient elution with NaCl is used. Elution with 10 mM NaCl recovers fractions containing conjugates with greater than 3 polymer strands PAO per IFN; elution with 50 mM NaCl recovers conjugates containing 1–2 strands; elution with 150 mM NaCl recovers unmodified IFN.

The temperature range for elution is between about 4° C. and about 25° C. Preferably, elution is carried out at a temperature of from about 6° C. to about 22° C. The elution of the PAO-αIFN fraction is detected by UV absorbance at 254 nm. Fraction collection may be achieved through simple time elution profiles. Other protein conjugates are similarly eluted.

6. Separation Of Positional Isomers

In accordance with the method, selected positional isomers of the protein-polymer are substantially separated from the reaction mixture, preferably after the mono-polymer conjugates have been separated from the other reactants. Due to the nature of the solution-based conjugation reactions, the conjugates are a heterogenous mixture of species which contain the polymer strand(s) attached at different sites on the protein. In any solution or reaction pool containing the conjugates, it is likely that substantially the entire spectrum of positional isomers will be present. In the case of αIFN-2b, preferred conjugate-containing solutions contain conjugates in which the polymer is attached at one of three available histidine residues such as His34 and optionally at one or more of Cys1, Lys31, Lys49, Lys83, Lys121, Lys131, and Lys134 of the alpha interferon-2b. When the reaction conditions and activated polymers described herein are employed, the attachment of the polymer at a His residue on alpha interferon 2b is at least about 50% of the total reaction pool, preferably at least about 75% and most preferably at least about 85% of the conjugates in the reaction pool. For example, when BTC-activated mPEG was used to form IFNα-2b conjugates, about 90% of the conjugates formed were the IFN-His-PEG positional isomers. When SC-PEG was used, about 55% of the conjugates formed were IFN-His-PEG positional isomers. Minor amounts of the other positional isomers were also found. It will be understood that alternative IF's as well as other proteins will provide alternative distributions of positional isomers, depending upon the amino acid sequence of the starting material.

Applicants have determined that within the spectrum of positional isomers for any protein conjugate, biological activity of individual positional isomers will differ. While Applicants are not bound by theory, it is believed that the differences in activity for the various positional isomers are not generally predictable. In view of this determination, the methods of the present invention allow the artisan to determine which isomers provide high amounts of particular positional isomers and means for isolating the particular positional isomers from the reaction pool is highly desirable.

Separation of the desired His-positional isomers or other positional isomers from the spectrum of conjugates can be effected by methods such as ion exchange chromatography. For purposes of the present invention, ion exchange includes cation and/or anion exchange. The conjugation process leading to the formation of the various positional isomers results in the individual position isomers being formed having different charge distributions. The difference in charge distributions can then be used to resolve (recover) any desired positional isomer using ion-exchange chromatography (i.e. cation and/or anion). For example, prior to separation, the spectrum of various positional isomers resulting from the conjugation reaction are placed in a buffer solution containing from about 0.5 to about 10% conjugates by weight. The buffer solutions contain one or more buffer salts selected from the non-limiting list of KCl, NaCl, $K_2HPO_4$, $KH_2PO_4$, $Na_2HPO_4$, $NaH2PO_4$, $NaHCO_3$, $NaBO_4$, $(NH_4)_2CO_3$ and glycine NAOH buffers are preferred for use in the present invention. The elution conditions will, of course, depend on the needs of the artisan and the positional isomer sought.

Generally, conventional high performance liquid chromatography techniques are followed. One such apparatus for effecting the desired separation is an HPLC system comprising a Mini-S cation exchange column, available from Pharmacia Biotech. It will be apparent to those of ordinary skill that alternative apparatus and columns such as an HPLC system comprising a SP-5PW column, available from Toso Haas, will also be of use to achieve the desired separation. A non-limiting list of suitable resins for carrying out the separation includes cation or anion exchange resins such as SP-, and CM-, Q- or DEAE Sepharose (from Pharmacia) and CM-, Q-Hyper D- from BioSepra.

As an illustrative example, a composition containing substantially pure IFNα2b-Hs-polymer conjugates, i.e. ≧90%, can be isolated from IFN-polymer conjugates in a reaction pool using chromatography columns such as gel filtration followed by cation exchange or anion exchange followed by cation exchange. Such techniques provide a composition containing at least about 85% IFNα2b-His34-polymer conjugates and preferably at least about 90% IFNα2b-His34-polymer conjugates. The remaining percentage of the compositions will include other positional isomers which will not appreciably detract from the therapeutic effectiveness of the desired substantially pure positional isomer. Other positional isomers of interferon or other proteins are similarly isolated. For other protein conjugates a similar separation technique is used. It will also be understood from the foregoing that linear and/or step gradient separation techniques are also useful in obtaining the conjugates corresponding to a particular peak. In addition, the conjugates associated with each peak can be isolated in this fashion, if desired. If necessary, the collected fractions can be re-injected into the chromatography apparatus with the same ratio of feed volume to column bed volume to increase the purity of the fraction collected. The substantially pure positional isomers can subjected to peptide sequencing in order to determine the amino acid residue modified.

As a further example of the techniques described above, specific IFNα-2b-polymer conjugates corresponding to particular peaks can be recovered using a cation exchange resin such as mini-S in a HPLC system. Each peak is purified on the cation exchange chromatography system using a linear gradient (A-40 mM sodium acetate, B-40 mM sodium acetate, 100 mM NaCl) at pH 4.7 to 5.3, wavelength 214 nanometers. Techniques using multiple isocratic steps of increasing concentration of the elution buffer, as discussed above, for the purpose of recovering the mono-polymer conjugates can also be adapted for recovery of the desired conjugates corresponding to a particular peak.

7. Effect Of Reaction pH Upon Positional Isomer Distribution

The process of the present invention takes advantage of the discovery that the site of polymer attachment on most proteins is influenced to a large extent by the pH of the reaction system. As the pH of the reaction solution is varied, the reactivity towards specific forms of activated polymers of the various functional groups such as alpha-amines, imidazoles and epsilon amines will vary. Typically, polymer conjugation reactions are carried out at basic pHs in order to maximize attachment at lysine epsilon amino groups. For example, Zalipsky et al. Biotech. & App. Biochem, Vol 15, p.100–114; (1992) evaluated the SC-PEG reagent for PEGylation and reported that the optimal reactivity was at about pH 9.3. The method of the present invention, however, includes conducting the reaction at significantly lower pH's in order to allow a substantial portion of the activated polymer strands to attach to histidine amino groups and de-emphasize, but not eliminate, lysine and N-terminus sites for attachment.

It has also been unexpectedly determined that the relative distribution of the positional isomers is largely dependent upon the pH at which the conjugation reaction is carried out. For example, shifting the pH from basic to slightly acidic pH (about 4.5 to 6.8) favors the formation of conjugates linked at His34 on IFNα2b, and to a lesser extent, the N-terminus (Cys1) and lysine residues. Using pH(8–10) during the conjugation reaction, on the other hand, favors the formation of lysine-related attachment sites, confirmed via cation exchange chromatography. Of course, when IFNα2b is not included, the His residue will be different. The reaction conditions nonetheless allow covalent attachment of an activated polymer to a His.

8. Pharmacokinetic Parameters

As pointed out above, preferred compositions of the present invention do not contain a heterogeneous mixture of polymer-IFN species in which the polymer strand(s) is/are attached at different sites on the interferon molecule. Thus, the compositions have predictable in vivo pharmacolinetic and bioactivity profiles which maximize the therapeutic effect of the conjugated protein.

In the case of IFNα, some preferred compositions are substantially pure PEG-His34-IFN positional isomers. The compositions retain at least about 20%, preferably at least about 35% and most preferably at least about 50% of the unmodified protein bioactivity. It will be understood that the amount of retained activity and length of circulating life will depend upon several factors including the protein, and the number and weight of the polymer strands attached to the protein.

9. Methods Of Treatment

Another aspect of the present invention provides methods of treatment for various medical conditions in mammals, preferably humans. The methods include administering an effective amount of a protein-polymer conjugate which has been prepared as described herein to a mammal in need of such treatment. The conjugates are useful for, among other things, treating conditions which are treated with the unmodified protein. For example, mammals in need of enzyme replacement therapy or blood factors can be given the substantially pure polymer conjugates containing the desired material. In the case of alpha interferon, interferon-susceptible conditions or conditions which would respond positively or favorably as these terms are known in the medical arts to interferon-based therapy.

Conditions that can be treated in accordance with the present invention are generally those that are susceptible to treatment with interferon alpha. For example, susceptible conditions include conditions which would respond positively or favorably as these terms are known in the medical arts to interferon alpha-based therapy. For purposes is of the invention, conditions that can be treated with interferon alpha therapy include those conditions in which treatment with an interferon alpha shows some efficacy, but which may not be treatable with interferon alpha because the negative side effects outweigh the benefits of the treatment. For example, side effects accompanying alpha therapy have virtually ruled out treatment of Epstein Barr virus using interferon alpha. Practice of the invention results in substantially reduced or eliminated side effects as compared to conventional interferon alpha treatment.

Exemplary conditions which can be treated with interferon include but are not limited to cell proliferation disorders, in particular cancer (e.g., hairy cell leukemia, Kaposi's sarcoma, chronic myelogenous leukemia, multiple myeloma, basal cell carcinoma and malignant melanoma, ovarian cancer, cutaneous T cell lymphoma), and viral infections. Without limitation, treatment with interferon may be used to treat conditions which would benefit from inhibiting the replication of interferon-sensitive viruses. Viral infections which may be treated in accordance with the invention include hepatitis A, hepatitis B, hepatitis C, other non-A/non-B hepatitis, herpes virus, Epstein-Parr virus (EBV), cytomegalovirus (CMV), herpes simplex, human herpes virus type 6 (HHV-6), papilloma, poxvirus, picornavirus, adenovirus, rhinovirus, human T lymphotropic virus-type 1 and 2 (HTLV-1/-2), human rotavirus, rabies, retroviruses including human immunodeficiency virus (HIV), encephalitis and respiratory viral infections. The method of the invention can also be used to modify various immune responses.

Variants of interferon alpha are currently approved in the United States and other countries for the treatment of hairy cell leukemia, venereal warts, Kaposi's Sarcoma, and chronic non-A/non-B hepatitis: interferon alpha-2b, marketed under the trade name INTRON® A (Schering Corporation, Kenilworth N.J.), and interferon alpha-2a, marketed under the trade name Roferon® A (Hoffinann-La Roche, Nutley, N.J.), and consensus interferon marketed under the trade name Infergen™ (Amgen, Thousand Oaks, Calif.). Since interferon alpha-2b, among all interferons, has the broadest approval throughout the world for treating chronic hepatitis C infection, it is most preferred for use in the treatment of chronic hepatitis C in accordance with practice of the invention.

Administration of the described dosages may be every other day, but is preferably once or twice a week. Doses are usually administered over at least a 24 week period by injection.

Administration of the dose can be intravenous, subcutaneous, intramuscular, or any other acceptable systemic method. Based on the judgment of the attending clinician, the amount of drug administered and the treatment regimen used will, of course, be dependent on the age, sex and medical history of the patient being treated, the neutrophil count (e.g. the severity of the neutropenia), the severity of the specific disease condition and the tolerance of the patient to the treatment as evidenced by local toxicity and by systemic side-effects. Dosage amount and frequency may be determined during initial screenings of neutrophil count.

Conventional pharmaceutical formulations can be also prepared using the substantially pure conjugate-containing compositions of the present invention. The formulations comprise a therapeutically effective amount of the substantially pure interferon-polymer conjugate composition together with pharmaceutically acceptable carriers. For example, adjuvants, diluents, preservatives and/or solubilizers, if needed, may be used in the practice of the invention. Pharmaceutical compositions of interferon including those of the present invention may include diluents of various buffers (e.g., Tris-HCl, acetate, phosphate) having a range of pH and ionic strength, carriers (e.g., human serum albumin), solubilizers (e.g., Tween, polysorbate), and preservatives (e.g., thimerosol, benzyl alcohol). See, for example, U.S. Pat. No. 4,496,537.

The amount of the substantially pure α-IFN polymer conjugate administered to treat the conditions described above is based on the IFN activity of the polymeric conjugate. It is an amount that is sufficient to significantly affect a positive clinical response. Although the clinical dose will cause some level of side effects in some patients, the maximal dose for mammals including humans is the highest dose that does not cause unmanageable clinically-important side effects. For purposes of the present invention, such clinically important side effects are those which would require cessation of therapy due to severe flu-like symptoms, central nervous system depression, severe gastrointestial disorders, alopecia, severe pruritus or rash. Substantial white and/or red blood cell and/or liver enzyme abnormalities or anemia-like conditions are also dose limiting.

Naturally, the dosages of the various αIFN compositions will vary somewhat depending upon the αIFN moiety and polymer selected. In general, however, the conjugate is administered in amounts ranging from about 100,000 to about several million $IU/m^2$ per day, based on the mammal's condition. The range set forth above is illustrative and those skilled in the art will determine the optimal dosing of the conjugate selected based on clinical experience and the treatment indication.

The pharmaceutical compositions may be in the form of a solution, suspension, tablet, capsule, lyophilzed powder or the like, prepared according to methods well known in the art. It is also contemplated that administration of such compositions will be chiefly by the parenteral route although oral or inhalation routes may also be used depending upon the needs of the artisan.

EXAMPLES

The following examples serve to provide further appreciation of the invention but are not meant in any way to restrict the effective scope of the invention.

Example 1

Figure 1:
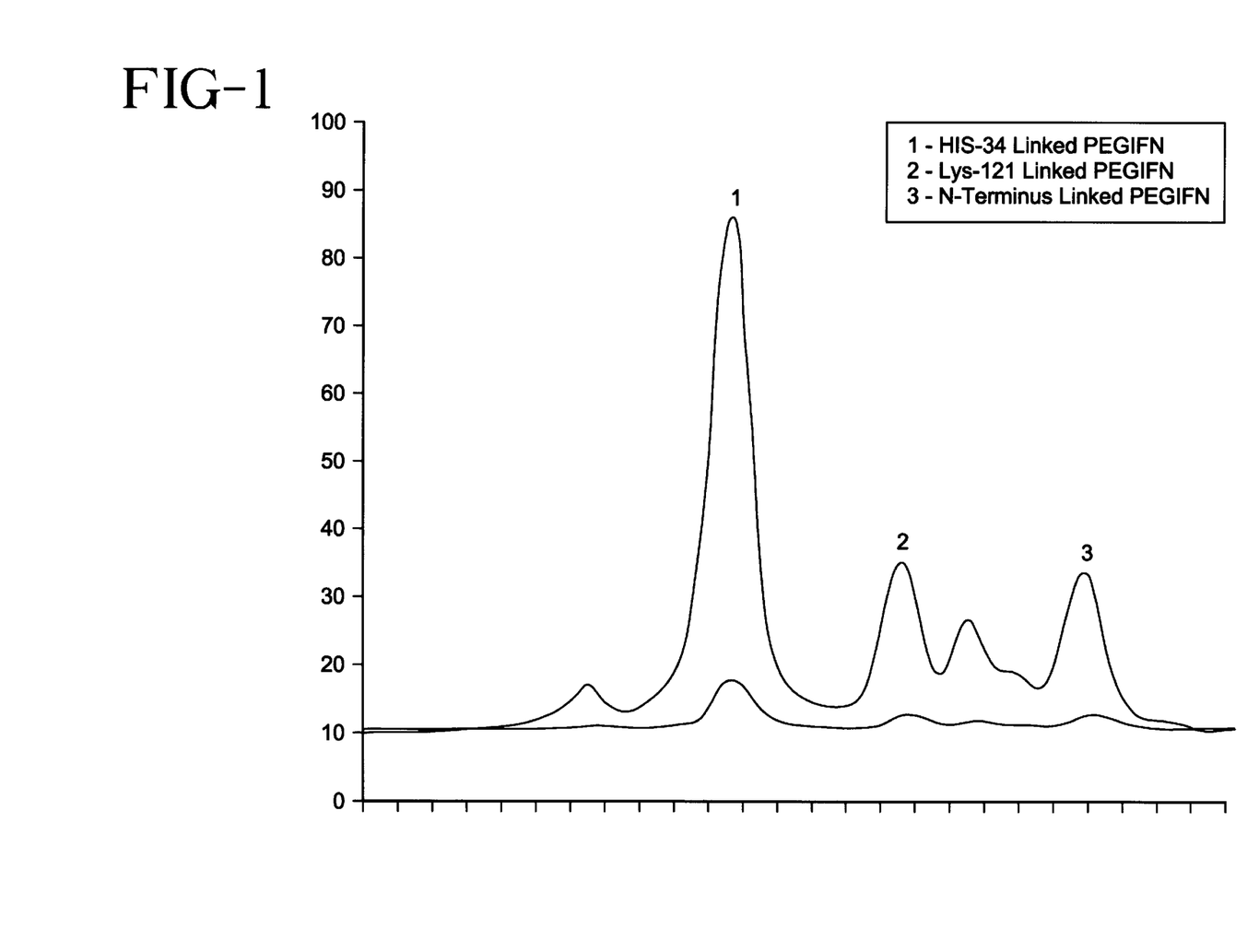
FIG. 1 is a chromatogram referred to in Example 1.

In this example, recombinant α-interferon 2b, (rαIFN), a product of the Schering Corporation, Kenilworth, N.J. was conjugated with activated polyethylene glycol-N-succinimidyl carbonate (SC-PEG), molecular weight 12,000 which was prepared as described in U.S. Pat. No. 5,122,614. The conjugation reaction was carried out at room temperature and at a pH of about 6.5. A ratio of 2.6 grams of $SC-PEG_{12,000}$ to 1 gram of IFN was used. The SC-PEG was added as a solid and the reaction was carried out at a temperature of about 4° C. At the end of the reaction, glycine was added to quench any residual PEGylation reagent. The product from the reaction was then purified using a Q-HyperD resin at pH 8 with salt elution to remove unreacted ingredients and multi-PEGylated species. The mono-PEG-IFN recovered from the Q-HyperD resin was about 55% His-34 linked PEG-IFN, 20% N-terminus, 12% Lysine-121 with the balance being Lys 131, Lys 1134, Lys 49 and Lys 83. This material containing the several positional isomers was then dialyzed against 20 mM acetate buffer at pH 4.9 and loaded onto a column packed with SP-Sepharose High Performance equilibrate with 10 mM acetate buffer at pH 4.9 (about 4 mg of material for 4 ml of resin). The material was eluted using a sodium chloride gradient (0–500 mM) in the acetate buffer. FIG. 1 shows the elution profile from the column. Peak 1 was found to be over 90% His34-linked PEG-IFN.

Example 2

In this Example, the conjugation process of Example 1 was repeated several times. Identification of the various positional isomers, however, was determined using anion exchange followed by cation exchange.

A Mini-S cation exchange column (Pharmacia Biotech) using a HPLC was employed to determine the sites of polymer attachment and identify the individual positional isomers. Mobile phase A included 10 mM sodium acetate pH 5.3 buffer and 25% 2-propanol. Mobile phase B contained 500 mM sodium chloride dissolved in mobile phase A. The flow rate was set at 0.5 ml/min and the eluted protein was detected at 214 nm. The individual PEG-IFN solutions were diluted with 10 mM sodium acetate pH 5.3, containing 2-propanol (5%) to 1 mg/ml protein concentration. Injection volumes ranged from 10 to 30 μl, depending upon the protein concentration.

The following linear gradient was used:

| Time (min) | A (%) | B (%) |
|---|---|---|
| 0 | 100 | 0 |
| 5 | 93 | 7 |
| 50 | 83 | 17 |
| 60 | 0 | 100 |
| 65 | 0 | 100 |
| 66 | 100 | 0 |
| 75 | 100 | 0 |

Figure 2:
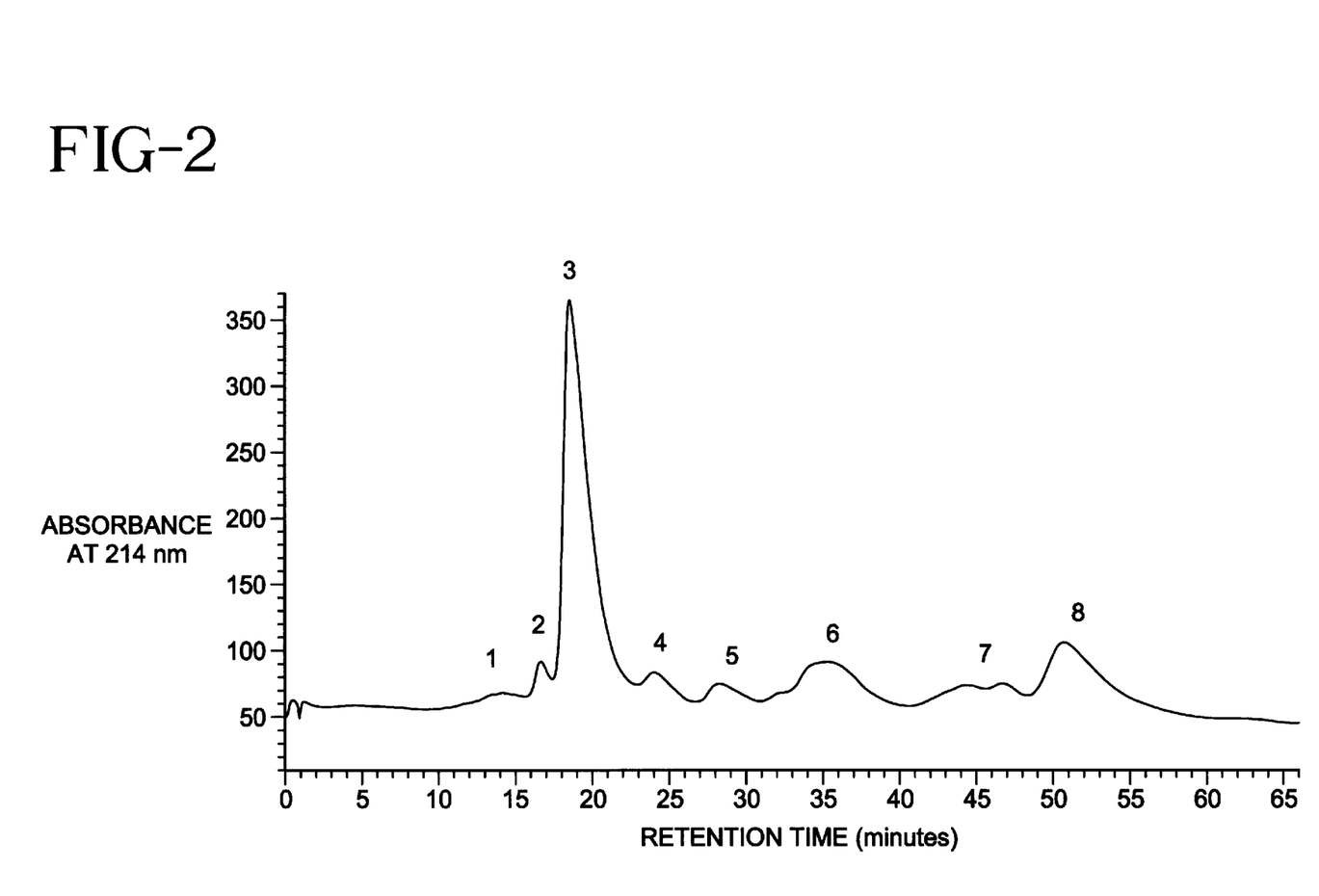
FIG. 2 is a chromatogram referred to in Example 2.

The results are provided in Table 1 below and graphically illustrated in FIG. 2. Referring now to the Figure, it can be seen that Peak 3 was determined to be the major component. Furthermore, the chromatography separation resulted in recovering major peaks of differing intensity. It is to be noted, however that the individual species, i.e. positional isomers, are not fully separated from one another in this system. For example, the fraction incorporating peak 3 was determined to contain about 90% His-34 positional isomer and about 10% of the Lys-31 positional isomer. Isolation and recovery of this fraction resulted in a composition containing substantially pure αIFN2b-His-34-PEG. There is some overlap in the positional isomer elution. It can be seen, however, that peak or a fraction 3 represented approximately 50% of the total PEG-interferon species.

TABLE 1

Area Percent Quantification of PEG-IFN Batches by Cation Exchange Chromotography

| Batch | Peak 2 | Peaks 3/4 | Peak 5 | Peak 6 | Peak 7a | Peak 7b | Peak 8 |
|---|---|---|---|---|---|---|---|
| 1 | 2.6 | 53.2 | 5.3 | 14.2 | 6.5 | 3.4 | 17.2 |
| 2 | 1.5 | 54.7 | 3.3 | 12.6 | 6.1 | 3.2 | 18.6 |
| 3 | 1.6 | 55.3 | 2.4 | 11.9 | 5.5 | 3.2 | 20.1 |
| 4 | 1.7 | 55.1 | 2.6 | 11.6 | 5.3 | 3.1 | 20.5 |
| 5 | 1.7 | 54.3 | 2.7 | 11.8 | 5.6 | 3.2 | 20.7 |
| 6 | 1.7 | 54.5 | 2.6 | 11.8 | 5.3 | 2.9 | 21.1 |
| 7 | 1.9 | 54.2 | 2.3 | 11.6 | 5.2 | 3.2 | 21.5 |

Main Peak Assignment: Peak 2: Lys-134 linked PEG-IFN; Peak ¾: His-34 linked PEG-IFN; Peak 6: Lys-121 linked PEG-IFN and Lys-131 linked PEG-IFN; Peak 8: Cys-1 linked PEG-IFN.

These results illustrate that a majority of the conjugates were found in peaks 3 and 4(His-34 linked PEG-IFN). The results also show that contrary to what was expected, most of the conjugates were formed by attaching the polymer to a histidine rather than one of the lysine amino groups.

Example 3

In this example, the various positional isomers identified in Example 2 were recovered using several cycles of a mono-S cation exchange. Each of the recovered chromatography fractions was then tested by CPE bioassay (antiviral activity). Table 2 below shows the bioactivity relative to native interferon (native=100%).

TABLE 2

RELATIVE BIOACTIVITY (IFN)

| Chromatography Fraction # | Relative Bioactivity* (%) |
|---|---|
| native IFN | 100 |
| 1 | 17.8 |
| 2 | 38.4 |
| 3 | 50.6 |
| 4 | 11.2 |
| 5 | 17.2 |
| 6 | 27.6 |
| 7 | 11.3 |
| 8 | 12.8 |

*Bioactivity as determined by CPE Bioassay

It can be seen from Table 2 that the His34 positional isomer site (which also includes a minor amount of Lys31) possesses the highest inherent bioactivity comparative to native interferon (51%). Thus, substantially pure compositions containing only this fraction, which is mainly the His-34 positional isomer, have advantages over conjugates containing the spectrum of positional isomers.

The fractions were then characterized using an enzymatic digestion analysis scheme using Trypsin and V-8 Protease followed by a size exclusion chromatography step for clean-up. The material was subjected to protein sequence analysis wherein the presence of the pegylated amino acid residue in the interferon peptide is inferred by a vacancy in the protein sequence. The characterization work revealed that the PEG is attached at eight different sites on the α-interferon-2b molecule: Cys 1, Lys31, His34, Lys49, Lys83, Lys121, Lys131 and Lys134. Details are provided below.

TABLE 3

| Chromatography Fraction # | Main Site of Pegylation |
|---|---|
| 1 | di-PEG? |
| 2 | Lys-134 |
| 3 | Lys-31 and His34 |
| 4 | Lys31 |
| 5 | not determined |
| 6 | Lys121 and Lys131 |
| 7 | Lys49, Lys83 |
| 8 | Cysteine residue/N-terminus Cys-1 |

Example 4

In this example, the procedure of Example 1 was repeated using benzotriazole carbonate-activated PEG (BTC-PEG) obtained from Shearwater Polymers, Inc. (molecular weight 12,000). In particular, IFNα-2b was reacted with BTC-PEG using a ratio of 2.6 grams of BTC per gram of IFN. The reaction was carried out at room temperature for 4 hours at a concentration of 2 mg interferon/ml before being quenched with glycine. A total of 60 mg of IFN was used. The reaction mixture was dialyzed against a gel filtration buffer containing 100 mM sodium phosphate buffer and 150 mM sodium chloride, pH 5.0. 5 ml of the dialyzed material was loaded onto a 200 ml Superdex 200 column equilibrated with the gel filtration buffer to separate the mono-PEG species from the multistranded species.

Before conducting the characterization of the various positional isomers, the mono-PEG-IFN reaction mixture was subjected to hydroxylamine sensitivity testing to determine the percentage of the conjugates were PEGylated at histidine sites, including the IFN-His34. Hydroxylamine is known to selectively cleave PEG from IFN histidines residues. An aliquot of each of the samples (50μl) was diluted with 0.45 ml of 10 mM sodium phosphate pH 7.0 An aliquot of this protein solution (150 μl) was treated with 150 μl of 0.5 M hydroxylamine and incubated at room temperature for 60 minutes. It was determined that over 90% of the conjugates were hydroxylamine-sensitive which indicates that over 90% of the material is His-linked-PEG interferon. Further characterization of the reaction mixture verified that His34 was the only histidine residue conjugated. HPLC chromatography of the Superdex 200 pool indicated that indeed His34 was the major PEGylation site. This was further confirmed by characterization of the final product using an enzymatic digestion analysis scheme similar to the procedure described in Example 3 which indicated that His34 was the major site of PEGylation. The specific activity of this positional isomer was found to be 89 MIU/mg.

The substantially pure IFN-His34-PEG conjugates were also recovered from the BTC-PEG-IFN reaction mixture using only one cycle of cation exchange chromatography. The reaction mixture was dialyzed against 40 mM sodium acetate buffer at pH 5.1. About 3.2 ml of the dialyzed reaction mixture was loaded onto 4 ml of an SP-5PW column and the His34-PEG-IFN peak was eluted using a NaCl gradient (0 to 500 mm)at pH 5.1. The His34-PEG-IFN purity of the product pool was at least 94%. The di-PEG-IFN in the pool was determined to be about 3–5%.

Examples 5–6

In these examples, the process of Example 4 was repeated using BTC-PEG (molecular weight 5,000, Ex.5, and 20,000, Ex. 6, respectively). The amount of His-PEG interferon for Example 5 was determined by hydroxylamine reaction to be about 90–95% while in Example 6 it was determined to be about 91%. Isolation of the various positional isomers of PEG-IFN using gel filtration was then carried out to remove non-mono-stranded conjugates The specific activity of the $PEG_{5,000}$-conjugates was determined to be about 119 MIU/mg while the $PEG_{20,000}$-His34 positional isomer specific activity was 89 MIU/mg.

Example 7

In this Example, the biological activity of individual positional isomers (His-34, Lys-121 and N-terminus) identified above was tested after incubation in normal human serum at 37° C. for up to 72 hours and compared to nonPEGylated native interferon. The results are shown in FIG. 3.

Figure 3:
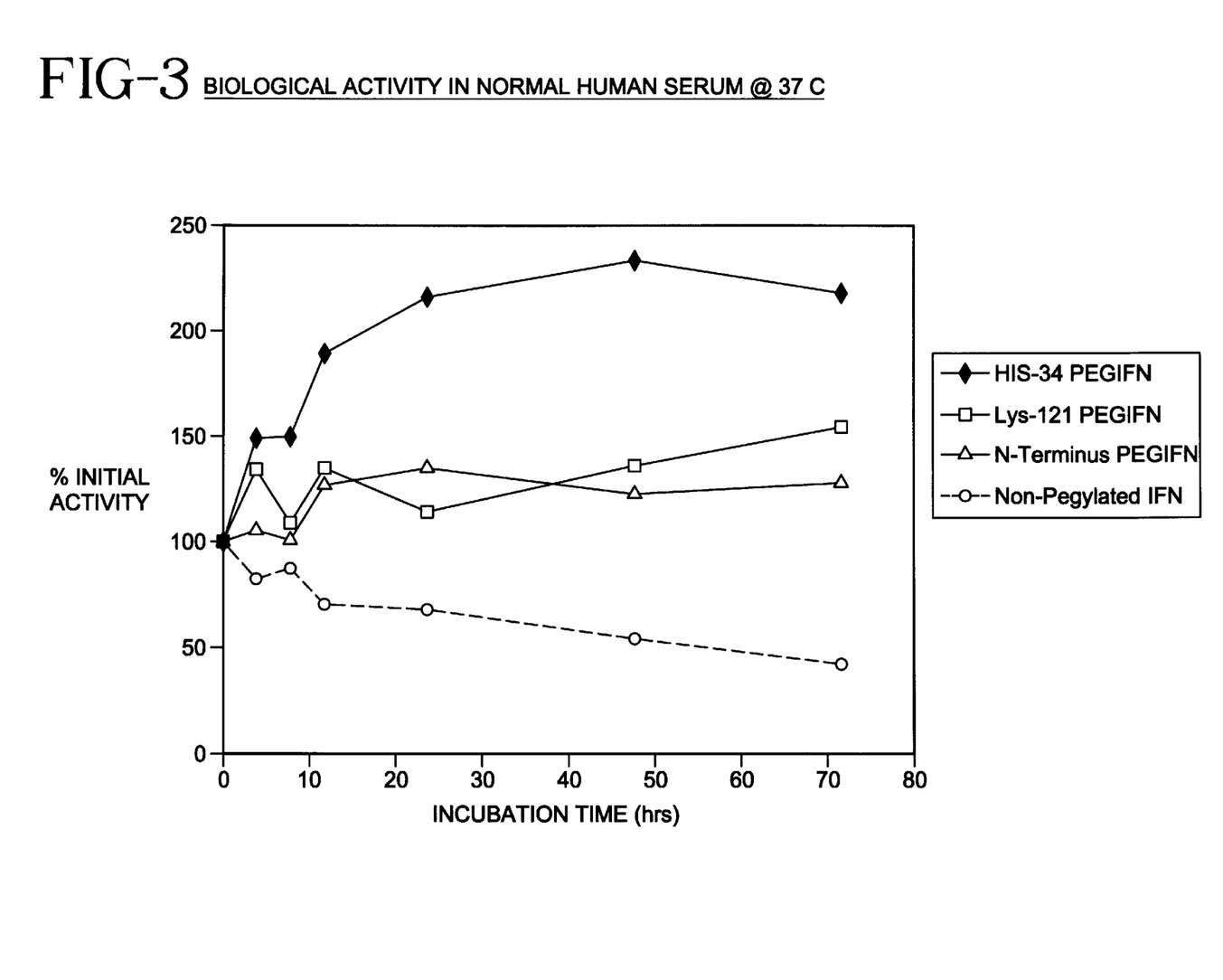
FIG. 3 is a graph referred to in Example 7 illustrating the biological activity of various positional isomers in normal human serum.

Referring now to FIG. 3, it can be seen that unexpectedly only the activity of the His-34 positional isomer increased over time while the activity of the other positional isomers remained relatively constant. The native interferon, on the other hand, demonstrates a predictable drop in activity over the observation period. While Applicants are not bound by theory, the increase in activity with the His34 linked material is believed to be related to the relatively slow hydrolysis of the His-PEG bond and subsequent release of free IFN. This figure shows the unique properties of the His-PEG bond in that under certain conditions it is weaker than Lys-PEG bonds and as such its breakdown provides an extended or "slow-release" delivery mechanism.

Examples 8–9

IL-10-Peg Conjugates

In these examples, the protein IL-10, a non-covalent homo dimer, was conjugated to BTC-PEG12,000(Ex.8) or SC-PEG12,000 (Ex. 9) at pH 6.5 in order to determine the degree of histidine-linked positional isomers in the resultant reaction pool. IL-10 has 3 available histidines.

The PEGylation procedures described above with regard to IFN were followed in order to carry out the conjugation. In particular, however, in each case a 2–3-fold molar excess of the activated polymer and gel filtration were used. Hydroxylamine sensitivity testing was done on each batch to determine the amount of His-containing positional isomers. The BTC-based conjugate was found to contain about 50% more hydroxylamine-labile conjugates than the SC-based conjugates. The specific bioactivity of the BTC-based conjugates was determined to be about 84% using the MC-9 bioassay. The SC-PEG-based conjugates were found to have a specific bioactivity of about 49%.

Other embodiments of the invention will be apparent to one skilled in the art from a consideration of this specification or practice of the invention disclosed herein. It is intended that the specification and examples be considered as exemplary only, with the true scope and spirit of the invention being indicated by the following claims.

What is claimed is:

1. A composition comprising protein-polymer conjugates, in which a majority of the conjugates comprise a polymer convalently conjugated to the protein only at a histidine residue.

2. The composition of claim 1, wherein said polymer comprises a polyalkylene oxide.

3. The composition of claim 2, wherein said polyalkylene oxide is a polyethylene glycol.

4. The composition of claim 3, wherein said polyethylene glycol is a monomethoxy-polyethylene glycol.

5. The composition of claim 1, wherein said polymer has a molecular weight of from about 200 to about 35,000.

6. The composition of claim 5, wherein said polymer has a molecular weight of from about 1,000 to about 25,000.

7. The composition of claim 6, wherein said polymer has a molecular weight of from about 2,000 to about 20,000.

8. A substantially pure protein-polymer conjugate, comprising a protein covalently conjugated to a polymer at a histidine residue on said protein, wherein said protein is an alpha interferon or IL-10.

9. The protein-polymer conjugate of claim 8, wherein said alpha interferon is interferon alpha 2b.

10. A method of preparing protein-polymer conjugates, wherein a protein is covalently conjugated to a polymer at a histidine residue on said protein, comprising:
  a) forming a plurality of protein-polymer conjugates by reacting a protein with a sufficient amount of an activated polymer under conditions sufficient to facilitate covalent attachment of said protein to said activated polymer; and
  b) substantially separating the protein-polymer conjugates containing a polymer conjugated to a histidine of the protein from said plurality of protein-polymer conjugates.

11. The method of claim 10, wherein said protein is alpha interferon or IL-10.

12. The method of claim 10, wherein said activated polymer is benzotriazole carbonate-activated polymer.

13. The method of claim 10, wherein said activated polymer is an oxycarbonyl-oxy-N-dicarboximide-activated polymer.

14. The method of claim 13, wherein said oxycarbonyl-oxy-N-dicarboximide is succinimidyl carbonate.

15. The method of claim 10, wherein said separating step is effected by gel filtration chromatography followed by ion exchange chromatography.

16. The method of claim 15, wherein said ion exchange chromatography is anion exchange chromatography.

17. The method of claim 10, wherein said separating step is effected by anion exchange chromatography followed by cation exchange chromatography.

18. The method of claim 10, wherein said reaction conditions comprise a pH of less than about 7.0.

19. The method of claim 18, wherein said reaction conditions comprise a pH of less than about 6.8.

20. The method of claim 19, wherein said reaction conditions comprise a pH of from about 4.5 to about 6.8.

21. The method of claim 11, wherein said alpha interferon is alpha interferon 2b.

22. The method of claim 10, wherein said activated polymer is present in a molar excess with respect to said protein.

23. The method of claim 10, wherein said polymer comprises a polyalkylene oxide.

24. The method of claim 23, wherein said polyalkylene oxide is a polyethylene glycol.

25. The method of claim 10, wherein said polymer has a molecular weight of from about 200 to about 35,000.

26. The method of claim 25, wherein said polymer has a molecular weight of from about 1,000 to about 25,000.

27. The method of claim 26, wherein said polymer has a molecular weight of from about 2,000 to about 20,000.

28. A method of treating a medical condition in mammals, comprising administering an effective amount of the composition of claim 1.

29. A composition comprising interferon-polymer conjugates prepared according to the method of claim 10, in which a majority of the conjugates comprise the polymer convalently conjugated to the protein only at a histidine residue.

30. A pharmaceutical composition comprising the composition of claim 1.

31. The protein-polymer conjugate of claim 8, wherein at least about 50% of said polymer is conjugated to said alpha interferon at the histidine residue on said alpha interferon.

32. The protein-polymer conjugate of claim 31, wherein at least about 75% of said polymer is conjugated to said alpha interferon at the histidine residue on said alpha interferon.

33. The protein-polymer conjugate of claim 32, wherein at least about 85% of said polymer is conjugated to said alpha interferon at the histidine residue on said alpha interferon.

34. The composition of claim 1, wherein said protein is an alpha interferon or IL-10.

35. The composition of claim 34, wherein said alpha interferon is interferon alpha 2b.

36. The composition of claim 1, wherein at least about 75% of said polymer is conjugated to said protein at a histidine residue on said protein.

37. The composition of claim 1, wherein at least about 85% of said polymer is conjugated to said protein at a histidine residue on said protein.

38. A method of treating a medical condition in mammals, comprising administering an effective amount of the conjugate of claim 8.

39. A pharmaceutical composition comprising the protein-polymer conjugate of claim 8.

* * * * *